United States Patent
Mesiwala

(10) Patent No.: US 9,693,876 B1
(45) Date of Patent: Jul. 4, 2017

(54) SPINAL FUSION IMPLANT AND RELATED METHODS

(71) Applicant: Ali H. Mesiwala, Claremont, CA (US)

(72) Inventor: Ali H. Mesiwala, Claremont, CA (US)

(*) Notice: Subject to any disclaimer, the term of this patent is extended or adjusted under 35 U.S.C. 154(b) by 0 days.

(21) Appl. No.: 13/854,945

(22) Filed: Apr. 1, 2013

Related U.S. Application Data

(60) Provisional application No. 61/618,640, filed on Mar. 30, 2012, provisional application No. 61/618,687, filed on Mar. 31, 2012.

(51) Int. Cl.
*A61F 2/44* (2006.01)

(52) U.S. Cl.
CPC .................. *A61F 2/447* (2013.01)

(58) Field of Classification Search
CPC .......... A61F 2/44–2/447; A61F 2/4611; A61F 2/4465; A61F 2002/30477
USPC .......... 623/17.11–17.16; 606/63, 68; 411/34, 411/37, 38
See application file for complete search history.

(56) References Cited

U.S. PATENT DOCUMENTS

| | | | |
|---|---|---|---|
| 4,554,914 A | 11/1985 | Kapp | |
| 4,599,086 A | 7/1986 | Doty | |
| 4,636,217 A | 1/1987 | Ogilvie | |
| 4,892,545 A | 1/1990 | Day | |
| 5,236,460 A | 8/1993 | Barber | |
| 5,522,899 A | 6/1996 | Michelson | |
| 5,658,335 A | 8/1997 | Allen | |
| 5,683,394 A | 11/1997 | Rinner | |
| 5,702,391 A | 12/1997 | Lin | |
| 5,713,904 A | 2/1998 | Errico | |
| 5,776,199 A | 7/1998 | Michelson | |
| 5,800,547 A | 9/1998 | Schmitz | |
| 5,800,550 A | 9/1998 | Sertich | |
| 5,849,004 A | 12/1998 | Bramlet | |
| 6,102,949 A | 8/2000 | Biedermann | |
| 6,102,950 A | 8/2000 | Vaccaro | |
| 6,176,882 B1 | 1/2001 | Biedermann | |
| 6,179,873 B1 | 1/2001 | Zientek | |
| 6,183,471 B1 | 2/2001 | Zucherman | |
| 6,183,474 B1 | 2/2001 | Bramlet | |
| 6,190,387 B1 | 2/2001 | Zucherman | |
| 6,214,050 B1 | 4/2001 | Huene | |
| 6,241,733 B1 | 6/2001 | Nicholson | |
| 6,302,914 B1 | 10/2001 | Michelson | |
| 6,371,987 B1 | 4/2002 | Weiland | |
| 6,436,140 B1 | 8/2002 | Liu | |
| 6,447,546 B1 * | 9/2002 | Bramlet et al. ............ 623/17.16 |

(Continued)

FOREIGN PATENT DOCUMENTS

| | | |
|---|---|---|
| AT | 395524 B | 6/1992 |
| EP | 4327054 C1 | 4/1995 |

(Continued)

*Primary Examiner* — Eduardo C Robert
*Assistant Examiner* — Michelle C Eckman
(74) *Attorney, Agent, or Firm* — Jeremy A. Smith; Bradley Arant Boult Cummings LLP

(57) ABSTRACT

The present invention relates generally to medical devices and methods for use in spinal surgery. In particular, the disclosed system relates to an intervertebral spinal implant assembly sized and dimensioned for the lumbar or cervical spine implantable via an anterior approach. The device includes an implant, bone fasteners, and instruments for delivering the implant and bone screws.

8 Claims, 7 Drawing Sheets

(56) References Cited

U.S. PATENT DOCUMENTS

| | | |
|---|---|---|
| 6,447,547 B1 | 9/2002 | Michelson |
| 6,454,805 B1 | 9/2002 | Baccelli |
| 6,527,803 B1 | 3/2003 | Crozet |
| 6,767,367 B1 | 7/2004 | Michelson |
| 6,770,096 B2 | 8/2004 | Bolger |
| 6,800,092 B1 | 10/2004 | Williams |
| 6,824,564 B2 | 11/2004 | Crozet |
| 7,153,325 B2 | 12/2006 | Kim |
| 7,166,130 B2 | 1/2007 | Ferree |
| 7,201,776 B2 | 4/2007 | Ferree |
| 7,232,463 B2 | 6/2007 | Falahee |
| 7,563,286 B2 | 7/2009 | Gerber |
| 7,594,932 B2 | 9/2009 | Aferzon |
| 7,662,187 B2 | 2/2010 | Zucherman |
| 7,704,279 B2 | 4/2010 | Moskowitz |
| 7,727,279 B2 | 6/2010 | Zipnick |
| 7,731,753 B2 | 6/2010 | Reo |
| 7,749,252 B2 | 7/2010 | Zucherman |
| 7,749,274 B2 | 7/2010 | Razian |
| 7,799,056 B2 | 9/2010 | Sankaran |
| 7,879,099 B2 | 2/2011 | Zipnick |
| 7,918,875 B2 | 4/2011 | Lins |
| 7,927,354 B2 | 4/2011 | Edidin |
| 7,931,674 B2 | 4/2011 | Zucherman |
| 7,959,652 B2 | 6/2011 | Zucherman |
| 7,998,211 B2 | 8/2011 | Baccelli |
| 8,021,428 B2 | 9/2011 | Bartish |
| 8,062,374 B2 | 11/2011 | Markworth |
| 8,070,812 B2 | 12/2011 | Keller |
| 8,075,593 B2 | 12/2011 | Hess |
| 8,080,062 B2 | 12/2011 | Armstrong |
| 8,100,972 B1 | 1/2012 | Bruffey |
| 8,105,358 B2 | 1/2012 | Phan |
| 8,114,131 B2 | 2/2012 | Kohm |
| 8,119,152 B2 | 2/2012 | Shikinami |
| 8,123,782 B2 | 2/2012 | Altarac |
| 8,142,479 B2 | 3/2012 | Hess |
| 8,157,842 B2 | 4/2012 | Phan |
| 8,167,950 B2 | 5/2012 | Aferzon |
| 8,172,878 B2 | 5/2012 | Yue |
| 8,182,539 B2 * | 5/2012 | Tyber et al. ............... 623/17.16 |
| 8,192,495 B2 | 6/2012 | Simpson |
| 8,197,513 B2 | 6/2012 | Fisher |
| 8,231,676 B2 | 7/2012 | Trudeau |
| 8,241,330 B2 | 8/2012 | Lamborne |
| 8,257,443 B2 | 9/2012 | Kamran |
| 8,262,698 B2 | 9/2012 | Anderson |
| 8,267,966 B2 | 9/2012 | McCormack |
| 8,267,997 B2 | 9/2012 | Colleran |
| 8,273,108 B2 | 9/2012 | Altarac |
| 8,292,922 B2 | 10/2012 | Altarac |
| 8,303,630 B2 | 11/2012 | Abdou |
| 8,313,528 B1 | 11/2012 | Wensel |
| 8,323,344 B2 | 12/2012 | Galley |
| 8,323,345 B2 | 12/2012 | Sledge |
| 8,328,870 B2 | 12/2012 | Patel |
| 8,333,804 B1 | 12/2012 | Wensel |
| 8,349,013 B2 | 1/2013 | Zucherman |
| 8,361,116 B2 | 1/2013 | Edmond |
| 8,361,152 B2 | 1/2013 | McCormack |
| 8,366,777 B2 | 2/2013 | Matthis |
| 8,377,130 B2 | 2/2013 | Moore |
| 8,377,133 B2 | 2/2013 | Yuan |
| 8,377,139 B2 * | 2/2013 | Laubert et al. ............ 623/17.16 |
| 8,382,839 B1 | 2/2013 | Wensel |
| 8,388,656 B2 | 3/2013 | Sheffer |
| 8,394,145 B2 | 3/2013 | Weiman |
| 8,425,528 B2 | 4/2013 | Berry |
| 8,454,623 B2 | 6/2013 | Patel |
| 8,460,385 B1 | 6/2013 | Wensel |
| 8,486,120 B2 | 7/2013 | Shimko |
| 8,491,656 B2 | 7/2013 | Schoedinger |
| 8,512,347 B2 | 8/2013 | McCormack |
| 8,512,409 B1 | 8/2013 | Mertens |
| 8,523,946 B1 | 9/2013 | Swann |
| 8,540,769 B2 | 9/2013 | Janowski |
| 8,545,562 B1 | 10/2013 | Materna |
| 8,545,563 B2 | 10/2013 | Brun |
| 8,551,175 B1 | 10/2013 | Wensel |
| 8,597,353 B2 | 12/2013 | Kana |
| 8,597,357 B2 | 12/2013 | Trudeau |
| 8,597,360 B2 | 12/2013 | McLuen |
| 8,613,747 B2 | 12/2013 | Altarac |
| 8,617,245 B2 | 12/2013 | Brett |
| 8,685,104 B2 | 4/2014 | Lee |
| 8,690,947 B2 | 4/2014 | Shikinami |
| 8,715,350 B2 | 5/2014 | Janowski |
| 8,740,948 B2 | 6/2014 | Reglos |
| 8,753,394 B2 | 6/2014 | Zipnick |
| 8,795,368 B2 | 8/2014 | Trieu |
| 2001/0020186 A1 | 9/2001 | Boyce |
| 2002/0165613 A1 | 11/2002 | Lin |
| 2004/0002769 A1 | 1/2004 | Ferree |
| 2004/0010312 A1 | 1/2004 | Enayati |
| 2005/0033429 A1 | 2/2005 | Kuo |
| 2005/0222681 A1 | 10/2005 | Richley |
| 2006/0069436 A1 | 3/2006 | Sutton |
| 2006/0079961 A1* | 4/2006 | Michelson ............... 623/17.11 |
| 2006/0085071 A1 | 4/2006 | Lechmann et al. ....... 623/17.11 |
| 2006/0206208 A1* | 9/2006 | Michelson ............... 623/17.11 |
| 2006/0241621 A1* | 10/2006 | Moskowitz et al. ............ 606/72 |
| 2006/0276899 A1 | 12/2006 | Zipnick |
| 2007/0050030 A1 | 3/2007 | Kim |
| 2007/0219635 A1* | 9/2007 | Mathieu et al. .......... 623/17.16 |
| 2007/0250167 A1* | 10/2007 | Bray ..................... A61F 2/4465 623/17.11 |
| 2007/0270961 A1 | 11/2007 | Ferguson |
| 2007/0288005 A1 | 12/2007 | Arnin |
| 2008/0051902 A1 | 2/2008 | Dwyer |
| 2008/0108990 A1 | 5/2008 | Mitchell |
| 2008/0133017 A1 | 6/2008 | Beyar |
| 2008/0177307 A1* | 7/2008 | Moskowitz et al. .......... 606/246 |
| 2008/0249569 A1* | 10/2008 | Waugh et al. ................ 606/249 |
| 2008/0249575 A1* | 10/2008 | Waugh et al. ................ 606/305 |
| 2008/0249625 A1* | 10/2008 | Waugh et al. .............. 623/17.16 |
| 2008/0281425 A1* | 11/2008 | Thalgott ............... A61F 2/4465 623/17.16 |
| 2008/0306596 A1* | 12/2008 | Jones et al. ............... 623/17.16 |
| 2009/0062917 A1* | 3/2009 | Foley et al. .............. 623/17.16 |
| 2009/0062921 A1* | 3/2009 | Michelson ............... 623/17.16 |
| 2009/0105830 A1* | 4/2009 | Jones et al. ............... 623/17.16 |
| 2009/0105831 A1* | 4/2009 | Jones et al. ............... 623/17.16 |
| 2009/0192613 A1* | 7/2009 | Wing et al. ............... 623/17.11 |
| 2009/0192615 A1* | 7/2009 | Tyber et al. .............. 623/17.16 |
| 2009/0210062 A1* | 8/2009 | Thalgott et al. .......... 623/17.16 |
| 2009/0210064 A1* | 8/2009 | Lechmann et al. ....... 623/17.16 |
| 2009/0216331 A1 | 8/2009 | Grotz |
| 2009/0234039 A1 | 9/2009 | Chuang |
| 2009/0234455 A1* | 9/2009 | Moskowitz et al. ....... 623/17.11 |
| 2009/0265007 A1* | 10/2009 | Colleran .................. 623/17.16 |
| 2010/0010633 A1 | 1/2010 | Kohm |
| 2010/0057206 A1* | 3/2010 | Duffield et al. ........... 623/17.16 |
| 2010/0087925 A1* | 4/2010 | Kostuik et al. ........... 623/17.16 |
| 2010/0106249 A1* | 4/2010 | Tyber et al. .............. 623/17.11 |
| 2010/0137989 A1* | 6/2010 | Armstrong et al. ....... 623/17.16 |
| 2010/0145459 A1* | 6/2010 | McDonough et al. .... 623/17.16 |
| 2010/0145460 A1* | 6/2010 | McDonough et al. .... 623/17.16 |
| 2010/0161057 A1* | 6/2010 | Berry et al. .............. 623/17.16 |
| 2010/0185289 A1* | 7/2010 | Kirwan et al. ............ 623/17.11 |
| 2010/0217393 A1* | 8/2010 | Theofilos ................. 623/17.11 |
| 2010/0234889 A1 | 9/2010 | Hess |
| 2010/0305704 A1* | 12/2010 | Messerli et al. .......... 623/17.16 |
| 2010/0312345 A1* | 12/2010 | Duffield et al. ........... 623/17.16 |
| 2010/0331986 A1 | 12/2010 | Shikinami |
| 2011/0009966 A1* | 1/2011 | Michelson ............... 623/17.11 |
| 2011/0046682 A1 | 2/2011 | Stephan |
| 2011/0087327 A1* | 4/2011 | Lechmann et al. ....... 623/17.11 |
| 2011/0098747 A1* | 4/2011 | Donner ................. A61B 17/70 606/264 |
| 2011/0118843 A1* | 5/2011 | Mathieu et al. .......... 623/17.11 |
| 2011/0125267 A1* | 5/2011 | Michelson ............... 623/17.11 |
| 2011/0160773 A1 | 6/2011 | Aschmann |
| 2011/0166656 A1* | 7/2011 | Thalgott et al. .......... 623/17.16 |
| 2011/0166657 A1* | 7/2011 | Thalgott et al. .......... 623/17.16 |

(56) References Cited

U.S. PATENT DOCUMENTS

| | | | |
|---|---|---|---|
| 2011/0166658 A1* | 7/2011 | Garber et al. | 623/17.16 |
| 2011/0196494 A1 | 8/2011 | Yedlicka | |
| 2011/0230971 A1* | 9/2011 | Donner | A61B 17/70 |
| | | | 623/17.16 |
| 2011/0276141 A1 | 11/2011 | Caratsch | |
| 2011/0301713 A1* | 12/2011 | Theofilos | 623/17.16 |
| 2011/0301714 A1* | 12/2011 | Theofilos | 623/17.16 |
| 2011/0313528 A1* | 12/2011 | Laubert et al. | 623/17.16 |
| 2012/0010714 A1* | 1/2012 | Moskowitz et al. | 623/17.16 |
| 2012/0016477 A1 | 1/2012 | Metcalf | |
| 2012/0071979 A1 | 3/2012 | Zipnick | |
| 2012/0078371 A1* | 3/2012 | Gamache et al. | 623/17.16 |
| 2012/0078373 A1* | 3/2012 | Gamache et al. | 623/17.16 |
| 2012/0089185 A1 | 4/2012 | Gabelberger | |
| 2012/0095559 A1 | 4/2012 | Woods | |
| 2012/0095561 A1 | 4/2012 | Voisard | |
| 2012/0101580 A1* | 4/2012 | Lechmann et al. | 623/17.16 |
| 2012/0101581 A1* | 4/2012 | Mathieu et al. | 623/17.16 |
| 2012/0109308 A1* | 5/2012 | Lechmann et al. | 623/17.16 |
| 2012/0109309 A1* | 5/2012 | Mathieu et al. | 623/17.16 |
| 2012/0109310 A1* | 5/2012 | Mathieu et al. | 623/17.16 |
| 2012/0109311 A1* | 5/2012 | Mathieu et al. | 623/17.16 |
| 2012/0109312 A1* | 5/2012 | Mathieu et al. | 623/17.16 |
| 2012/0109313 A1* | 5/2012 | Mathieu et al. | 623/17.16 |
| 2012/0130495 A1* | 5/2012 | Duffield et al. | 623/17.16 |
| 2012/0130496 A1* | 5/2012 | Duffield et al. | 623/17.16 |
| 2012/0158149 A1* | 6/2012 | Kostuik et al. | 623/17.16 |
| 2012/0185048 A1* | 7/2012 | Phelps | 623/17.16 |
| 2012/0197401 A1* | 8/2012 | Duncan et al. | 623/17.16 |
| 2012/0203348 A1* | 8/2012 | Michelson | 623/17.16 |
| 2012/0209385 A1* | 8/2012 | Aferzon | 623/17.16 |
| 2012/0215318 A1* | 8/2012 | Michelson | 623/17.16 |
| 2012/0245690 A1* | 9/2012 | Cowan, Jr. | A61F 2/4465 |
| | | | 623/17.16 |
| 2012/0265259 A1* | 10/2012 | LPosta et al. | 606/86 A |
| 2012/0271423 A1* | 10/2012 | Wallenstein et al. | 623/17.16 |
| 2012/0277870 A1* | 11/2012 | Wolters et al. | 623/17.16 |
| 2012/0277871 A1* | 11/2012 | Theofilos | 623/17.16 |
| 2012/0316649 A1* | 12/2012 | Johnston et al. | 623/17.16 |
| 2012/0330419 A1* | 12/2012 | Moskowitz et al. | 623/17.16 |
| 2013/0006367 A1* | 1/2013 | Bucci | 623/17.16 |
| 2013/0018470 A1* | 1/2013 | Moskowitz et al. | 623/17.16 |
| 2013/0018471 A1* | 1/2013 | Davenport et al. | 623/17.16 |
| 2013/0023992 A1* | 1/2013 | Moskowitz et al. | 623/17.16 |
| 2013/0053891 A1* | 2/2013 | Hawkins et al. | 606/264 |
| 2013/0053902 A1 | 2/2013 | Trudeau | |
| 2013/0053967 A1* | 2/2013 | Sournac et al. | 623/17.16 |
| 2013/0060336 A1* | 3/2013 | Hooper et al. | 623/17.11 |
| 2013/0060339 A1* | 3/2013 | Duffield et al. | 623/17.16 |
| 2013/0066428 A1* | 3/2013 | Biedermann et al. | 623/17.16 |
| 2013/0073044 A1* | 3/2013 | Gamache | 623/17.16 |
| 2013/0150969 A1 | 6/2013 | Zipnick | |
| 2013/0150970 A1* | 6/2013 | Thaiyananthan | 623/17.16 |
| 2013/0166032 A1* | 6/2013 | McDonough et al. | 623/17.16 |
| 2013/0190874 A1* | 7/2013 | Glazer | 623/17.11 |
| 2013/0218276 A1* | 8/2013 | Fiechter et al. | 623/17.16 |
| 2013/0218277 A1* | 8/2013 | Blain et al. | 623/17.16 |
| 2013/0218279 A1* | 8/2013 | Michelson | 623/17.16 |
| 2013/0226300 A1* | 8/2013 | Chataigner et al. | 623/17.16 |
| 2013/0231749 A1* | 9/2013 | Armstrong et al. | 623/17.16 |
| 2013/0238095 A1* | 9/2013 | Pavento et al. | 623/17.16 |
| 2013/0245767 A1* | 9/2013 | Lee et al. | 623/17.16 |
| 2013/0268076 A1 | 10/2013 | Carlson | |
| 2013/0274881 A1 | 10/2013 | Arginteanu | |
| 2013/0274883 A1 | 10/2013 | McLuen | |
| 2013/0338776 A1 | 12/2013 | Jones | |
| 2014/0085536 A1 | 3/2014 | Wang | |
| 2014/0088715 A1 | 3/2014 | Ciupik | |
| 2014/0277513 A1 | 9/2014 | Fessler | |

FOREIGN PATENT DOCUMENTS

| | | |
|---|---|---|
| EP | 0697200 A1 | 2/1996 |
| EP | 1338257 A1 | 8/2003 |
| EP | 1374809 A1 | 1/2004 |
| EP | 1104665 A1 | 3/2004 |
| EP | 2116212 A1 | 11/2009 |
| EP | 1925272 A1 | 1/2010 |
| EP | 2368529 A1 | 9/2011 |
| EP | 2510904 A1 | 10/2012 |
| EP | 2638880 A1 | 9/2013 |
| FR | 2722679 A1 | 1/1996 |
| FR | 2779941 A1 | 12/1999 |
| FR | 2794968 A1 | 12/2000 |
| FR | 2880795 A1 | 7/2006 |
| FR | 2930426 A1 | 10/2009 |
| FR | 2943529 A1 | 10/2010 |
| FR | 2943530 A1 | 10/2010 |
| FR | 2965169 A1 | 3/2012 |
| FR | 2975586 A1 | 11/2012 |
| FR | 2979227 A1 | 3/2013 |
| FR | 2992166 A1 | 12/2013 |
| JP | 2003230583 A | 8/2003 |
| JP | 2010051651 A | 3/2010 |
| KR | 20010020293 A | 2/2001 |
| KR | 20020033648 A | 5/2002 |
| KR | 20120000905 A | 1/2012 |
| WO | WO-9000037 A1 | 1/1990 |
| WO | WO-0074605 A1 | 12/2000 |
| WO | WO-0103614 A1 | 1/2001 |
| WO | WO-2006066992 A1 | 6/2006 |
| WO | WO-2006102269 A2 | 9/2006 |
| WO | WO-2006134262 A1 | 12/2006 |
| WO | WO-2008044057 A1 | 4/2008 |
| WO | WO-2008112607 A2 | 9/2008 |
| WO | WO-2009086010 A2 | 7/2009 |
| WO | WO-2010037926 A1 | 4/2010 |
| WO | WO-2010092893 A1 | 8/2010 |
| WO | WO-2010116511 A1 | 10/2010 |
| WO | WO-2010127390 A1 | 11/2010 |
| WO | WO-2010141910 A2 | 12/2010 |
| WO | WO-2011092399 A1 | 8/2011 |
| WO | WO-2011141869 A1 | 11/2011 |
| WO | WO-2012047289 A1 | 4/2012 |
| WO | WO-2012117312 A2 | 9/2012 |
| WO | WO-2012141715 A1 | 10/2012 |
| WO | WO-2013008111 A1 | 1/2013 |

* cited by examiner

SPINAL FUSION IMPLANT AND RELATED METHODS

CROSS REFERENCE TO RELATED APPLICATIONS

This application claims the benefit of the filing date of U.S. Provisional Patent Application No. 61/618,640 which was filed on Mar. 30, 2012 and U.S. Provisional Patent Application No. 61/618,687 which was filed on Mar. 31, 2012. The contents of U.S. Application Nos. 61/618,640 and 61/618,687 are incorporated by reference as part of this application.

FIELD

The present invention relates generally to spinal surgery and, more particularly, to a device for spinal fusion comprising a spinal fusion implant of non-bone construction to be introduced into any variety of spinal target sites.

BACKGROUND

Currently there are nearly 500,000 spine lumbar and cervical fusion procedures are performed each year in the United States. One of the causes of back pain and disability results from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space. Introducing the intervertebral implant from an anterior approach serves to restore the height between adjacent vertebrae ("disc height"), which reduces if not eliminates neural impingement commonly associated with a damaged or diseased disc.

SUMMARY

In a preferred aspect, the spinal fusion implant includes a body configured for implantation via an anterior approach (e.g. anterior lumbar interbody fusion or anterior cervical discectomy and fusion) between a superior and inferior vertebra, having a top surface and a bottom surface, an anterior height and a posterior height, and a fusion aperture defined by an anterior wall, a posterior wall, and first and second lateral walls. In some implementations, the anterior height of the body is greater than the posterior height of the body, such that the top surface creates a posterior-to-anterior angle relative to the horizontal axis. The posterior-to-anterior angle may be between 0° and 15°. In some implementations, the body will have a medial support extending from the anterior wall to the posterior wall through the fusion aperture. The medial support is defined by a first and second lateral wall, having a top and bottom surface, and an aperture extending through the anterior wall to receive a drive screw. The medial support has a horizontal axis extending from the midpoint of the anterior wall through the midpoint of the posterior wall.

The body may be constructed of radiolucent, non-bone material. At least one of the top surface and bottom surface may include anti-migration features. The body may also include at least one radiopaque marker. In some implementations, the body may include an engagement groove in the lateral walls dimensioned to receive a gripping element of an inserter.

The spinal fusion implant includes a drive screw aperture at the midpoint of the anterior wall, extending through the anterior wall into the implant along the horizontal axis. The drive screw aperture is dimensioned to receive a drive screw for insertion into the implant. The drive screw has a head, a shank and a collar disposed between the head and shank. The collar and shank of the drive screw may be at least partially threaded.

The spinal fusion implant also includes a plurality of fastener apertures extending through the anterior wall at oblique angles relative to a horizontal axis. Each of the fastener apertures is dimensioned to receive a bone fastener for insertion into one of the superior or inferior vertebrae. The bone fasteners may have a head, a shank and a collar disposed between the head and shank. The bone fasteners are of a material that can flex or deform to accommodate the aperture angle upon insertion, but is still rigid enough to penetrate the superior and inferior vertebral processes.

The bone fasteners are connected such that they can be driven into the implant with the screwing in of the drive screw. This may be accomplished with an intermediary plate or a drive screw collar. The intermediary plate or drive screw collar has a driving screw aperture for receiving a drive screw. The drive screw will be used to advance bone spikes through the implant apertures by pulling the intermediary plate to the implant.

Implementations may include one or more of the following features. For example, fastener apertures extending through the anterior wall of the implant body may at angles between 35° and 55° relative to the horizontal axis. Preferably, the fastener apertures extend through the anterior wall of the body at a 45° angle relative to the horizontal axis.

The fastener apertures may also extend through the anterior wall at angles oblique to the longitudinal axis. In some implementations, the angles oblique to the longitudinal axis may be divergent. Preferably, the angles are between 5° and 15° relative to the longitudinal axis. More preferably, the fastener apertures extend through the anterior wall at a 12° angle relative to the longitudinal axis.

In a preferred embodiment, the spinal fusion implant includes four fastener apertures and one drive screw aperture. Two of the apertures may be dimensioned to receive bone fasteners for insertion into the inferior vertebra, two of the apertures may be dimensioned to receive bone fasteners for insertion into the superior vertebra, and the drive screw aperture is dimensioned to receive a drive screw that can be fully contained by the implant.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The anterior lumbar interbody implant disclosed herein boasts a variety of inventive features and components that warrant patent protection, both individually and in combination.

The implant consists of a top surface and a bottom surface, an anterior height and a posterior height, and a fusion aperture defined by an anterior wall, a posterior wall, and first and second lateral walls. In one embodiment, the anterior height of the body is greater than the posterior height of the body, such that the top surface creates a posterior-to-anterior angle relative to the horizontal axis. The implant anterior wall may have a central drive screw aperture and a plurality of bone fastener apertures. In one embodiment, there will be two upper bone fastener apertures and two lower bone fastener apertures, designed to receive bone fasteners. In the one embodiment the bone fasteners are spikes.

Figure 1:
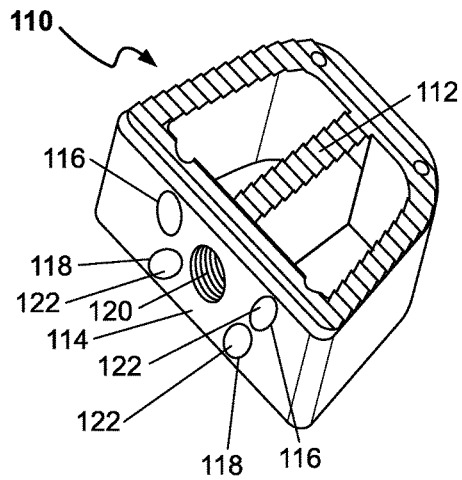
FIG. 1 is a perspective view of a spinal implant, according to one example embodiment.
Figure 3:
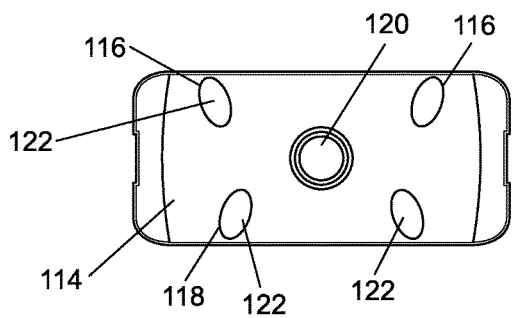
FIG. 3 is a view of the anterior wall face of spinal implant of FIG. 1.
Figure 8:
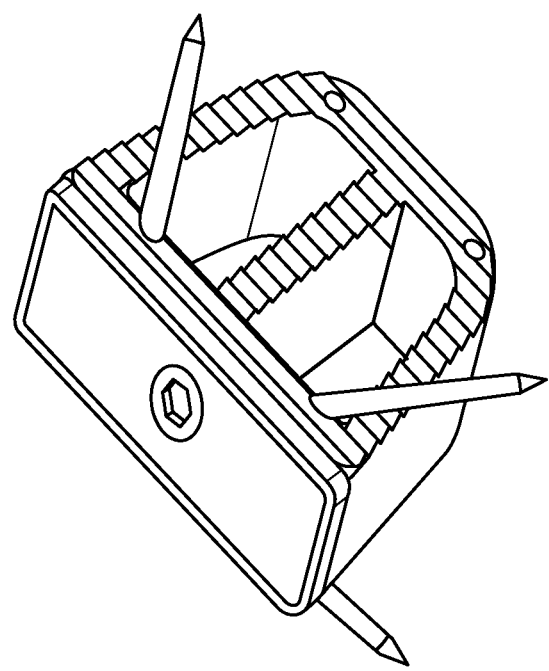
FIG. 8 is a perspective view of the spinal implant assembly of FIG. 7 and the implant of FIG. 1 with the drive screw of FIG. 4 fully inserted in the implant.
Figure 9:
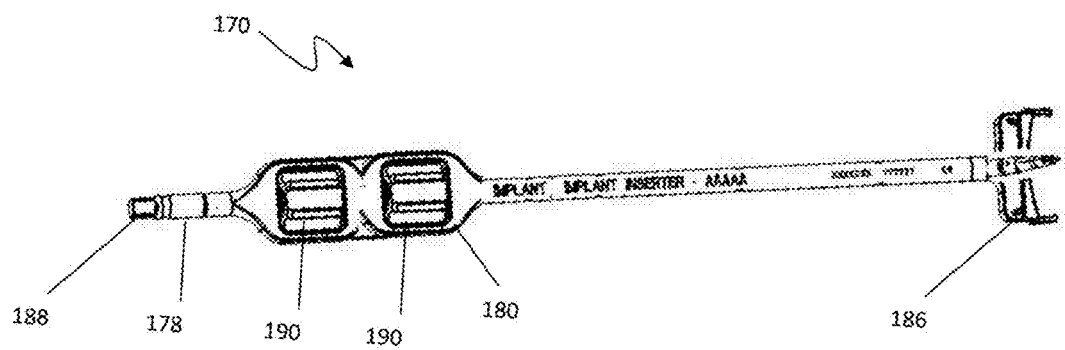
FIG. 9 is an insertion instrument according to a first embodiment.

As best appreciated in FIGS. 1, 3, and 8, the upper spike apertures 116 pass through the anterior side 114 at an angle such that when the spikes 140 are inserted into the upper spike apertures 116, they extend from the implant 110 at an angle and penetrate into the vertebral body superior to the implant 110. By way of example only, the upper spike apertures 116 may be angled such that the spikes 140 penetrate into the vertebral body at an angle between 35 and 55 degrees, and preferably 45 degrees. Lower spike apertures 118 also pass through the anterior side 114 at an angle, but in the opposite direction of the upper spike apertures 116. Thus, when the spike 140 is inserted into the lower spike apertures 118, it extends from the implant 110 at an angle and penetrates the vertebral body inferior to the implant 110. By way of example, the lower spike apertures 118 may be angled such that the lower spikes 140 penetrate into the vertebral body at an angle between 35 and 55 degrees, and preferably 45 degrees. The lateral spike apertures 116, 118 may also be angled such that the distal end of the spikes 140 diverge away from each other. By way of example, the nail apertures may be oriented such that the spikes are angled laterally between 5 and 15 degrees, and preferably 12 degrees. The medial spike apertures 116, 118 may also be angled such that the distal end of the spikes 140 diverge away from each other. By way of example, the spike apertures may be oriented such that the spikes are angled laterally between 5 and 15 degrees, and preferably 10 degrees.

Figure 2:
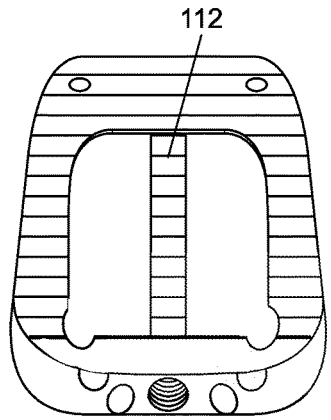
FIG. 2 is a top view of the spinal implant of FIG. 1.

As demonstrated in FIGS. 1-3, a drive screw aperture 120 extends through the anterior wall into the implant. The drive screw aperture 120 is located at the midpoint of the anterior wall 114 and, according to one embodiment, is threaded to receive the drive screw. In one embodiment, the drive screw aperture extends from the anterior wall into a medial support 112 extending from the anterior wall to the posterior wall. The medial support 112 is defined by a top and bottom surface, a first and second lateral wall, the anterior and posterior wall of the implant body, and has a threaded aperture to accommodate the drive screw 130. The drive screw aperture 120 is centered along a horizontal axis that extends from the mid-point of the anterior wall to the mid-point of the posterior wall. The body of the drive screw, when in the final locked position, is fully contained within the implant.

Figure 6:
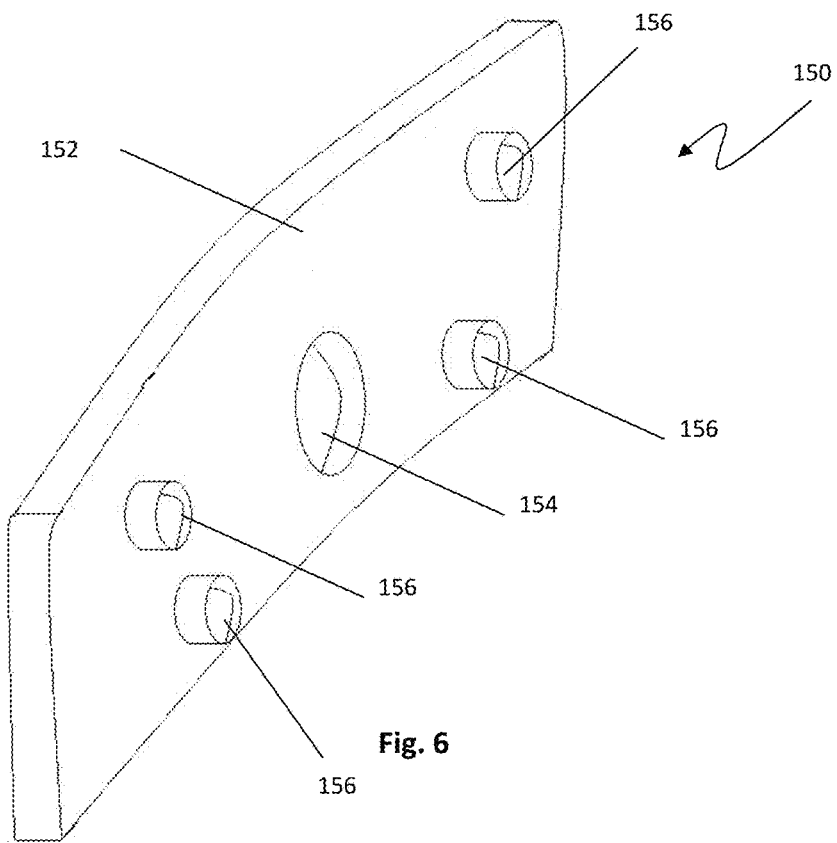
FIG. 6 is a perspective view of the posterior facing side of an intermediary plate, according to one example embodiment, for use with the spinal implant of FIG. 1.
Figure 7:
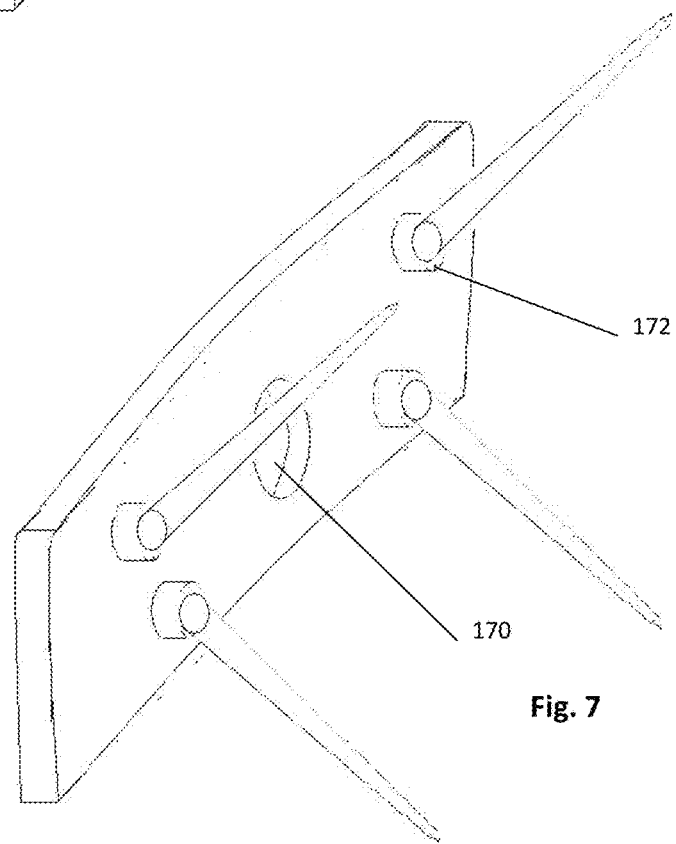
FIG. 7 is a perspective view of FIG. 6 with four bone nails attached with a ball joint connection to the posterior face.

The spikes may be connected to the drive screw by any method such that the spikes may be advanced into the implant without the spikes rotating while turning the drive screw into the implant. The use of a collar around the neck of the drive screw or an intermediary plate is contemplated, but any composition may be used to achieve this purpose. As best seen in FIGS. 6 and 7, the spikes are flexibly connected to the intermediary plate 150 and the intermediary plate has a central aperture 154 through which the drive screw can rotate freely. The intermediary plate consists of an anterior surface and a posterior surface. The anterior surface is smooth to reduce abrasion with the spinal anatomy. The posterior surface 152 has features to hold the heads of the bone nails and is designed to interface with the anterior surface of the implant. In one embodiment, the posterior surface has four sockets 156 to hold the heads of four spikes in a ball and socket configuration. The intermediary plate can be of any shape and size, but the preferred embodiment is such that the intermediary plate matches the shape of the anterior side of the implant and has minimal thickness, while maintaining structural integrity.

Figure 5:
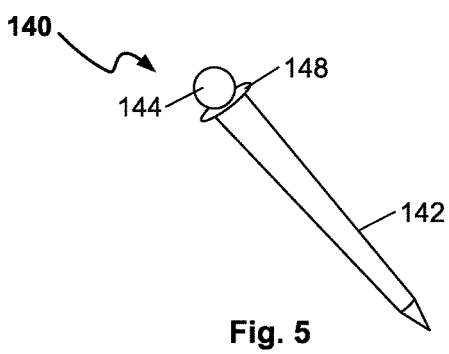
FIG. 5 is a perspective view of the bone nail, according to one example embodiment, for use with the spinal implant of FIG. 1.

With reference to FIG. 5, there is shown a spike 140 for use with the spinal fusion implant 110. The spike 140 has a shaft 142, a head 144, and may have a neck or rim 148. The head is such that it can be flexibly or rigidly connected to the intermediary plate. As seen in FIG. 7, in one embodiment, the head of the spike 144 is connected to the intermediary plate with a ball and socket joint. The spike head 144 may act as the ball in the ball joint. The spike is of a material sufficiently flexible to expand from a fully sheathed position prior to implant to an expanded position at the angle of the implant bone nail aperture when fully deployed. While the spike material is flexible enough to expand through the bone, it also must be rigid enough such that it can penetrate the superior and inferior vertebral processes with minimal deformity.

Figure 4:
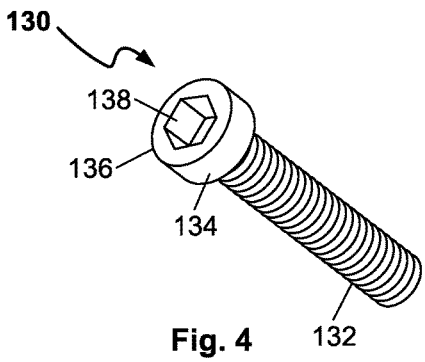
FIG. 4 is a perspective view of a drive screw, according to one example embodiment, for use with the spinal implant of FIG. 1.

With reference to FIG. 4, there is shown a drive screw 130 for use with the spinal fusion implant 110. The drive screw has a head 134, a threaded shaft 132, and may have a neck separating the head and shaft. The drive screw head 134 further comprises a rim 136 and a tooling recess/engagement mechanism 138, for engaging an insertion tool. The body of the drive screw will fit through the intermediary plate aperture and the diameter of the rim 136 is slightly larger than the diameter of the intermediary plate aperture such that the drive screw head 134 cannot fully pass through the intermediary plate aperture. The drive screw 130 draws the intermediary plate with it as the drive screw enters the implant and holds the plate to the implant, by way of the rim 136, when in the final locked position. As appreciated in FIG. 8, when in the final locked position, the drive screw holds the intermediary plate to the implant and is fully inserted in the implant. With the intermediary plate connected to the implant, the spikes will protrude from the bone fastener apertures such that they extend superior and inferior to the implant to engage vertebral bodies through the endplates, fixing the implant in place.

The present invention may include a plurality of inserters which provide the user with a suite of choices for implanting the implant 110. According to a broad aspect of the present invention, the insertion instruments are capable of gripping and releasing the implant and screwing the drive screw into the implant. As described in FIGS. 9-14, one embodiment of the insertion instrument consists of a handle, an outer elongated tubular shaft, an intermediary inserter shaft, an inner drive shaft, two thumbwheels, and gripping elements.

The handle 178 is generally disposed at the proximal end of the insertion instrument 170. The handle 178 may be further equipped with a universal connector 188 to allow the attachment of accessories for ease of handling of the insertion instrument 170 (e.g. a straight handle, or a T-handle, not shown). The handle 178 is fixed to the thumbwheel housing 180 allowing easy handling by the user. By way of example, the thumbwheel housing 180 holds the two thumbwheels 190, a set screw 192, and at least one spacer 194. Because the handle 178 is fixed, the user has easy access to the thumbwheels 190 and can stably turn the thumbwheels 190 relative to the thumbwheel housing 180. Additionally, the relative orientation of the thumbwheel housing 180 to the handle 178 orients the user with respect to the distal insertion head 186. The inserter shaft 184 is attached to one of the thumbwheels 190 and is freely rotatable with low friction due to the spacer 194. The inner drive shaft 185 is attached to the other thumbwheel and is freely rotatable with low friction due to a spacer. The user may then employ the first thumbwheel 190 to rotate the inserter shaft 184 thereby advancing it towards distal inserter head 186. The user may employ the second thumbwheel to rotate the drive shaft, thereby turning drive the drive screw into the implant.

Figure 10:
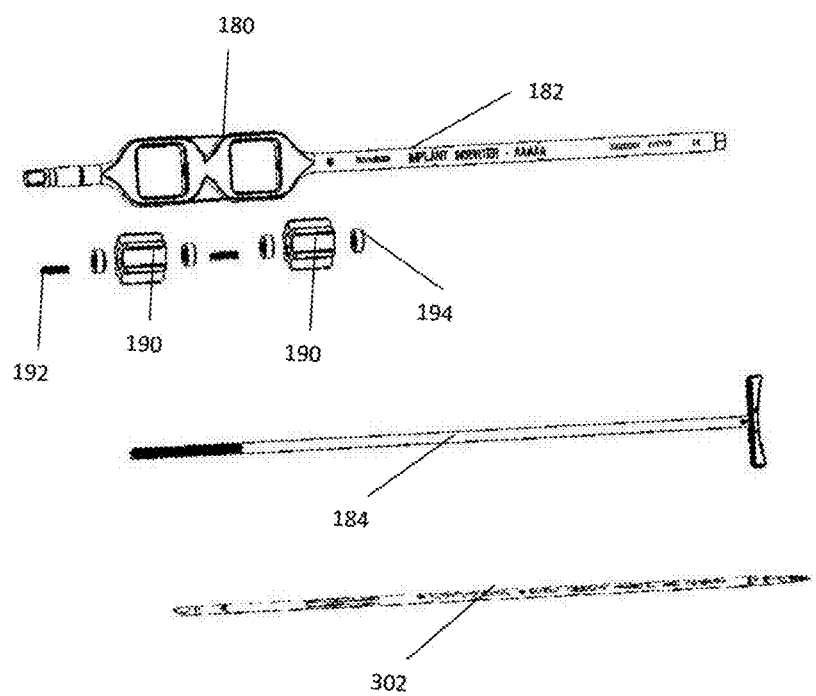
FIG. 10 is an exploded view of the insertion instrument of FIG. 9.
Figure 11:
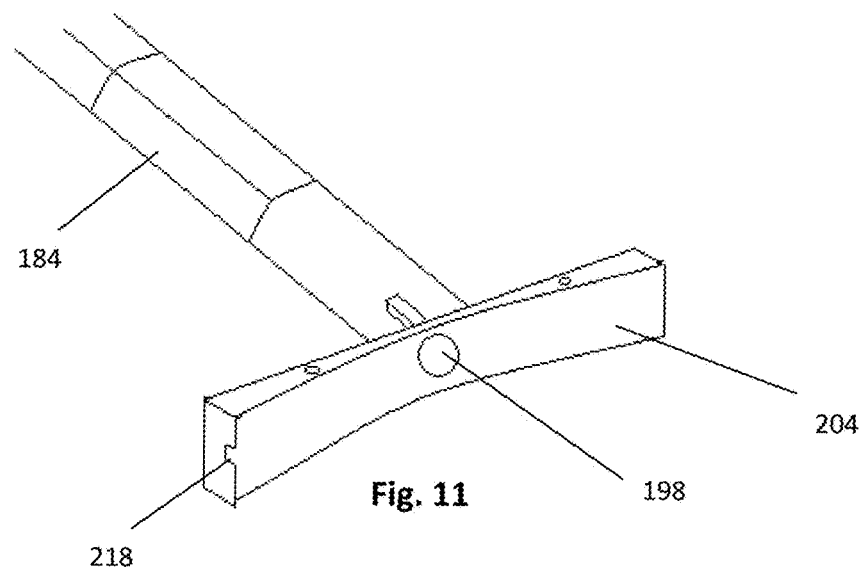
FIG. 11 is a perspective view of the inserter shaft and head.
Figure 12:
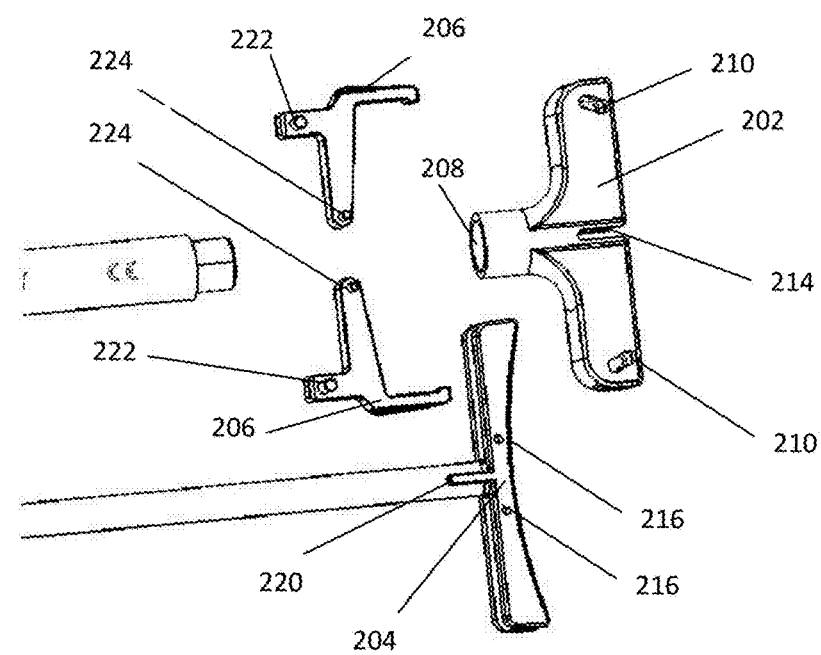
FIG. 12 is an exploded view of the insertion head of the insertion instrument of FIG. 9 and the driver.
Figure 12:
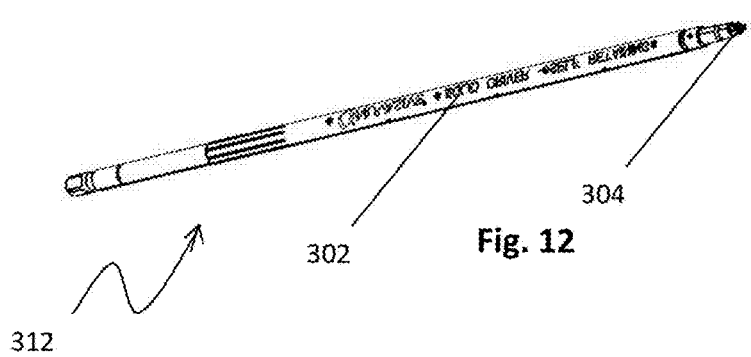
Figure 13:
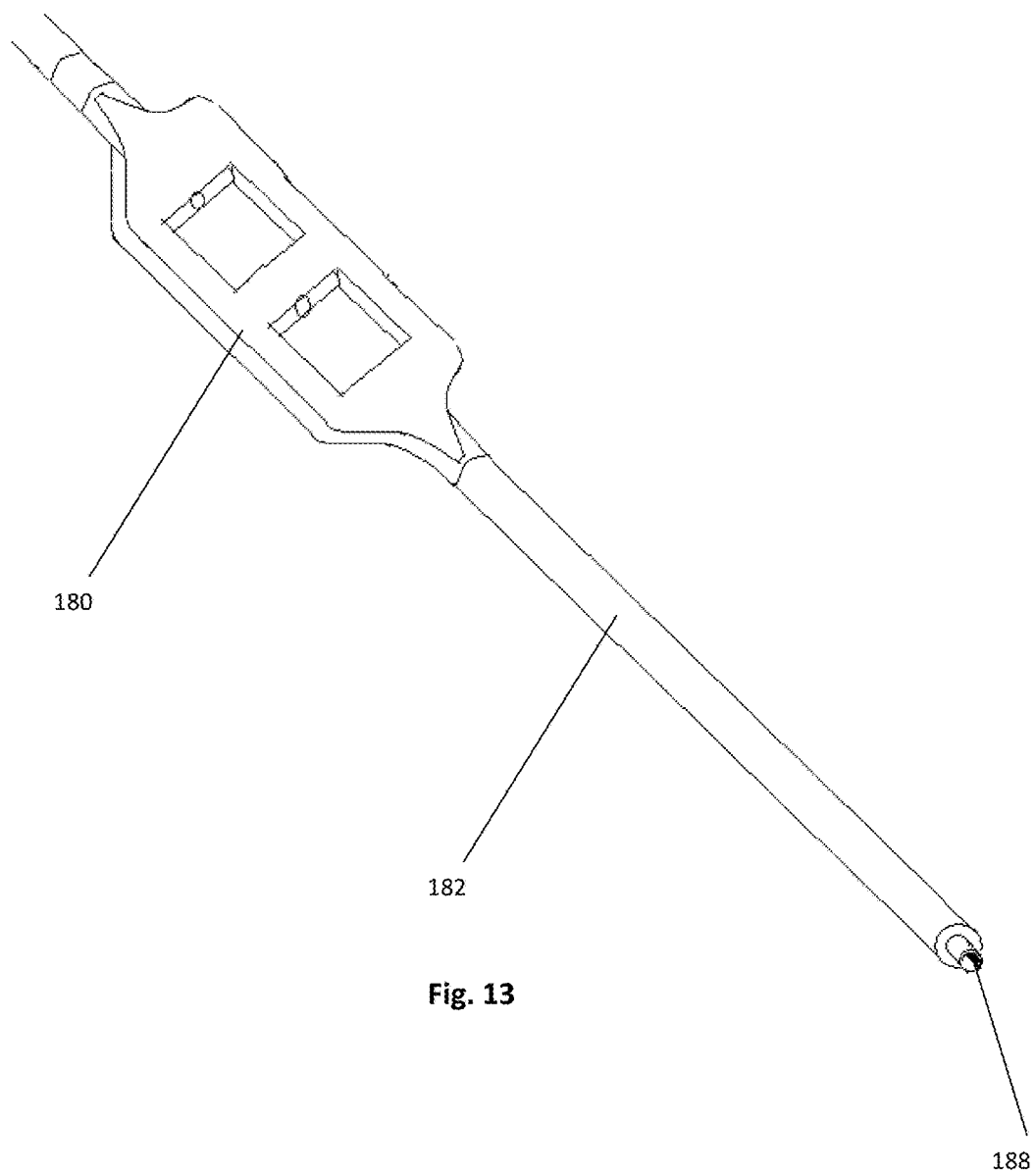
FIG. 13 is a perspective view of the outer shaft and housing of the insertion instrument of FIG. 9.
Figure 14:
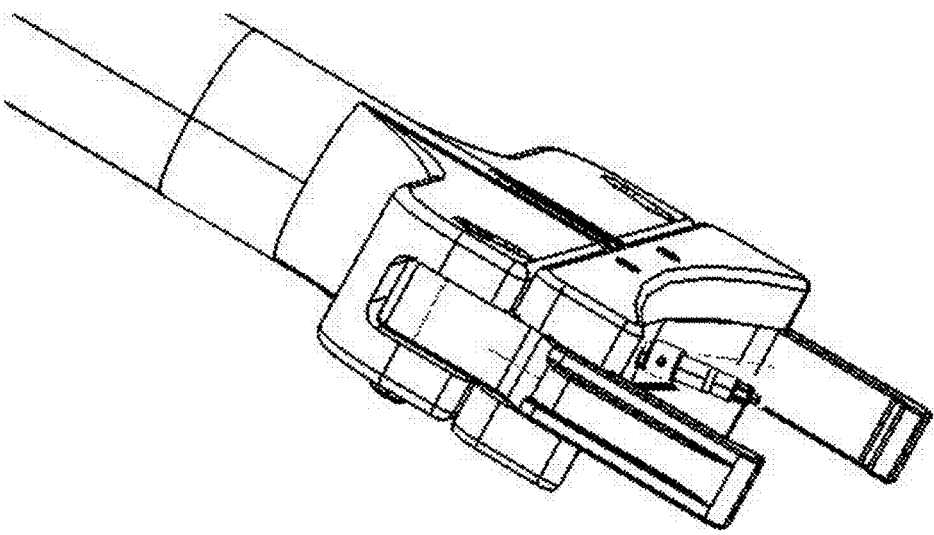
FIG. 14 is perspective view of the assembled head of the insertion instrument.

Best seen in FIGS. 10 and 13, the outer elongated tubular shaft 182 is generally cylindrical and of a length sufficient to allow the device to span from the surgical target site to a location sufficiently outside the patient's body so the handle 178 and thumbwheel housing 180 can be easily accessed by a clinician or a complimentary controlling device. The elongated tubular shaft 182 is dimensioned to receive a spring 196 and the proximal ends of both the inserter shaft 184 and the inner drive shaft 185 into the inner bore 188 of the elongate tubular element 182.

FIGS. 9-14 detail an insertion instrument 170 according to a first embodiment of the present invention, preferably adapted for insertion from an anterior approach. The distal inserter head 186 is comprised of a fixed inserter base 202 extending generally perpendicularly from gripping arm to rotate in relation to the actuating member 204. Each lateral channel 218 is sized and dimensioned such that the lateral aspect of each gripping arm 206 is seated within the lateral channel 218. The central protrusion 220 is sized and dimensioned to be slideably received by central slot 214 on the inserter base 202. As the central protrusion 220 of the actuating member 204 is being advanced by the inserter shaft 184, it travels along the appropriate path within the central slot 214.

The two gripping arms 206 each contain a laterally-disposed guide post 222, a medially-disposed pivot pin 224, and a terminal engagement hook 226. Gripping arms 206 are seated within the inserter base 202 via the lateral channels 212 and seated within the actuating member 204 via the lateral channels 218. Gripping arms 206 are attached to the actuating member 204 via the pivot pins 224 received within the pin-receiving apertures 216 on the actuating member 204. The gripping arms 206 are pivotably disposed within the fixed inserter base 202 via the guide posts 222 positioned within the guide slots 210.

The rotation of the first thumbwheel 190 in the clockwise direction causes the inserter shaft 184 to retreat within the elongate tube member 182, which will result in pulling the actuating member 204 closer towards the inserter base 202. This movement will cause the gripping arms 206 to pivot about the pivot pins 224 of the gripping arms 206. When the inserter shaft 184 is fully retracted within the elongate tubular member 182 and the actuating member 204 has reached a final position with the inserter base 202, the gripping arms 206 are releaseably engaged to the spinal fusion implant 110 such that the insertion instrument 170 is stabilized relative to the spinal fusion implant 110. Once the implant 110 has been successfully inserted into the disc space, the second thumbwheel 190 is rotated, thereby drive the drive screw and bone nails into the implant 110. Once the drive screw is fully inserted into the implant, the first thumbwheel is rotated in a counter clockwise direction, thereby de-coupling the inserter from the implant.

According to a broad aspect, the inner drive shaft may be comprised of an elongate shaft portion 302 coupled to a distal drive portion 304. The distal end of the guided straight driver 312 is placed within the drive screw engagement mechanism 138. The rotation of the thumbwheel 190 in the clockwise direction causes the driver 312 to advance within the inserter shaft 184 and drives the screw 126 into the implant.

It is expected that a standard anterior approach to the spine is performed per surgeon preference. An annulotomy template is placed onto the disc space and a centering pin is placed, penetrating the annulus at the midline. The centering pin may have a length of between 10 and 25 mm, preferably 20 mm. Anterior-posterior fluoroscopy may be used to verify midline placement of the centering pin. Additionally, lateral fluoroscopy may be used to check depth. A surgical knife is used to cut the annulus, using the lateral edges of the annulotomy template as a guide. Additionally, if the spinal fusion implant is to be further used as a partial vertebral body replacement, the necessary resections may also be made to the vertebral body or bodies. A desired trial may be implanted into the annulotomy cut and gently impacted into the disc space such that it is subflush, preferably approximately 2 mm from the anterior lip of the vertebral body. The implant corresponding to the appropriate trial side should be selected and attached to the proper size implant inserter (as described above), and filled with an appropriate graft material. The implant is gently impacted into the disc space. Lateral fluoroscopy may be used to confirm proper implant placement. Once the implant is placed, the screw is driven into the implant and the nails are driven into the superior and inferior vertebral processes.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A spinal fusion implant comprising:
   a body having a top surface, a bottom surface, a fusion aperture defined by an anterior wall, a posterior wall, and first and second lateral side walls, said anterior wall including a threaded aperture extending therethrough;
   a plurality of bone fasteners;
   a drive screw; and
   a substantially flat plate having an anterior surface and a posterior surface and being coupled to the plurality of bone fasteners such that the bone fasteners extend from a posterior surface of the plate, wherein the plate includes an aperture extending from the anterior surface and exiting exclusively through posterior surface configured to align with the threaded aperture of the anterior wall of the body and receive the drive screw therethrough;
   wherein the anterior wall of the body comprises a plurality of bone fastener apertures extending through the interior of the body of the implant and exiting through one of the top and bottom surface, each of said apertures configured to receive a bone fastener therethrough, and wherein the plurality of bone fasteners are coupled to the plate prior to insertion of the plurality of bone fasteners and the drive screw into the spinal fusion implant, and the plurality of bone fasteners are configured to deploy through the spinal fusion implant as the drive screw is inserted and advanced into the threaded hole in the anterior wall of the spinal fusion implant.

2. The spinal fusion implant of claim 1, wherein the plurality of bone fasteners are configured to be deployed through the spinal fusion implant without rotating.

3. The spinal fusion implant of claim 1, wherein the plurality of bone fasteners are spikes.

4. The spinal fusion implant of claim 1, wherein the plurality of bone fasteners are coupled to the drive screw via a collar.

5. The spinal fusion implant of claim 1, wherein the plurality of bone fastener apertures extend through the anterior wall of the body at an angle that is oblique to a horizontal plane of the spinal fusion implant.

6. The spinal fusion implant of claim 1, wherein the anterior wall has a first height and the posterior wall has a second height, and wherein the first height is greater than the second height.

7. The spinal fusion implant of claim 1, wherein the fusion aperture is divided by a medial support extending from the anterior wall to the posterior wall.

8. The spinal fusion implant of claim 7, wherein the medial support further comprises a drive screw aperture configured to receive the drive screw.

\* \* \* \* \*